United States Patent [19]

Saglio

[11] Patent Number: 4,604,897
[45] Date of Patent: Aug. 12, 1986

[54] MULTITRANSDUCER ULTRASONIC PROBE WITH TRANSDUCERS OF DIFFERENT SIZES

[75] Inventor: Robert Saglio, Antony, France

[73] Assignee: Commissariat a l'Energie Atomique, Paris, France

[21] Appl. No.: 636,003

[22] Filed: Jul. 30, 1984

[30] Foreign Application Priority Data

Aug. 1, 1983 [FR] France ............................ 83 12641

[51] Int. Cl.$^4$ ............................................. G01N 29/04
[52] U.S. Cl. ......................................... 73/626; 73/625; 73/641; 367/105
[58] Field of Search ................ 181/111, 112; 367/105; 73/625, 626, 641, 606

[56] References Cited

U.S. PATENT DOCUMENTS

| 4,161,121 | 7/1979 | Zitelli et al. | 73/626 |
| 4,235,111 | 11/1980 | Hassler | 367/105 |
| 4,276,779 | 7/1981 | Davis, Jr. | 73/626 |
| 4,307,613 | 12/1981 | Fox | 73/626 |
| 4,329,876 | 5/1982 | Chen | 73/618 |
| 4,478,085 | 10/1984 | Sasaki | 73/625 |

FOREIGN PATENT DOCUMENTS

| 2051645 | 4/1971 | France . |
| 2243435 | 4/1975 | France . |
| 2298921 | 8/1976 | France . |
| 2453437 | 10/1980 | France . |

Primary Examiner—Howard A. Birmiel
Attorney, Agent, or Firm—Michael N. Meller

[57] ABSTRACT

A multitransducer ultrasonic probe having transducers of different sizes for the nondestructive testing of mechanical parts. The probe has at least one line of M transmitter and/or receiver ultrasonic transducers, a control unit for the activation of at least one group of m juxtaposed transducers, selected from the M transducers and for the displacement of the activated portion of the probe after each activation. The M transducers all have different sizes and are arranged in monotonic manner in accordance with their sizes, the sizes being determined so as to scan an object to be inspected with a redundancy rate which is independent of the depth of the locus to be inspected.

14 Claims, 6 Drawing Figures

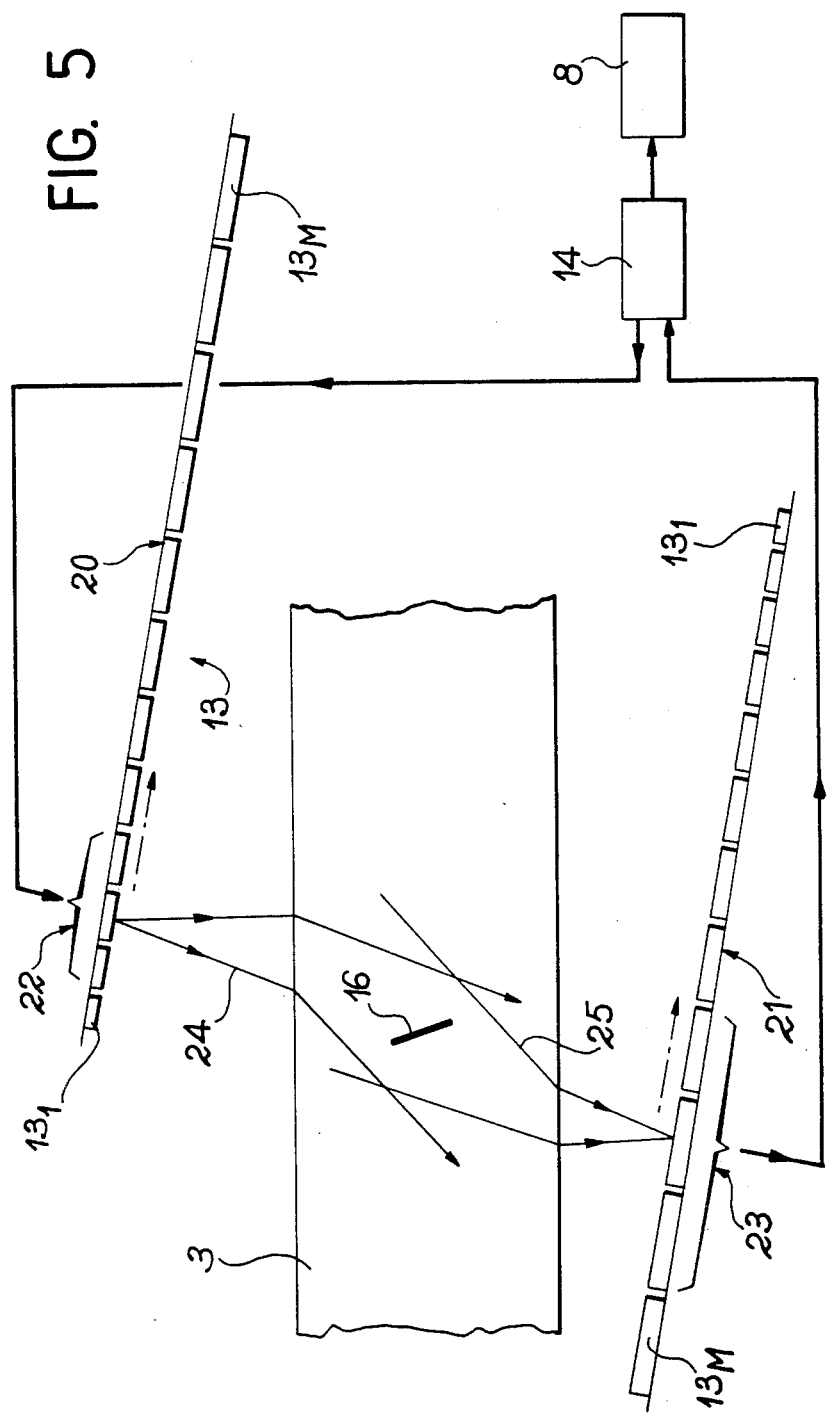

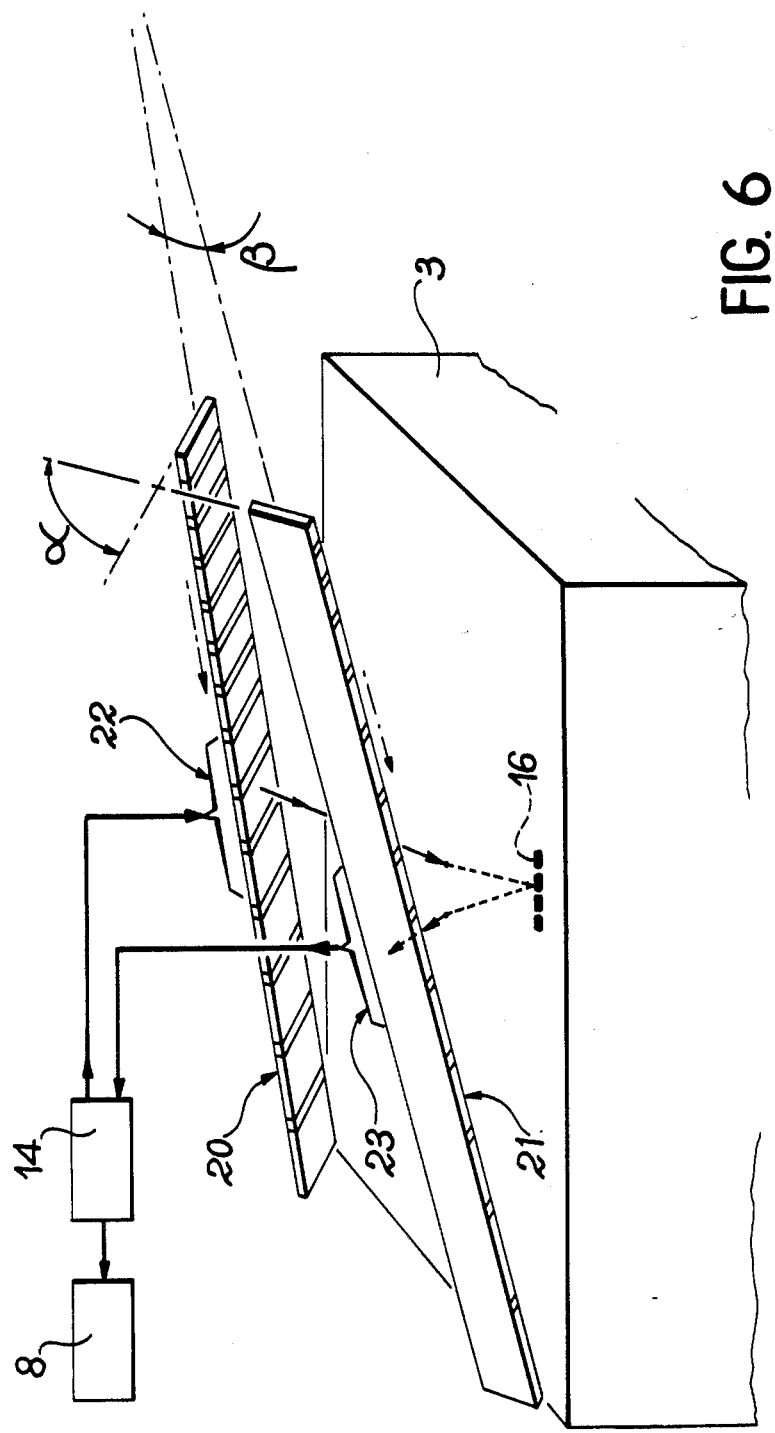

MULTITRANSDUCER ULTRASONIC PROBE WITH TRANSDUCERS OF DIFFERENT SIZES

BACKGROUND OF THE INVENTION

The present invention relates to an ultrasonic multitransducer probe with transducers of different sizes and is more particularly used in the non-destructive testing of mechanical parts.

Numerous ultrasonic multitransducer probes are known. They are all formed from geometrically identical transducers of the same size. In exemplified manner, FIG. 1 diagrammatically shows a known probe. For example, it is intended for use in the inspection or testing of a weld 2 by means of which two parts 3a and 3b are joined to one another, so as to form a single part 3. The probe shown in FIG. 1 comprises a linear strip 4 of M juxtaposed transmitter-receiver ultrasonic transducers 5, which are directed towards the part 3 to be inspected. The strip 4 is inclined relative to the surface 6 of part 3, the weld 2 being perpendicular thereto. Strip 4 is electrically connected to means 7 for activating a group 9 of m juxtaposed transducers of strips 4, so as to make them function firstly as ultrasonic transmitters and then as ultrasonic receivers. The said group of activated transducers is then displaced by an integral number of transducers, said number being e.g. equal to 1, so as to scan the complete strip 4 and thus investigate the part 3 in depthwise manner and consequently weld 2 over its entire height. The means 7 making it possible to displace the group of activated transducers is electrically connected to means 8 for the volume display of part 3.

Transducers 5 are all of the same size, i.e. have the same receiving-transmitting zone width (considered in the lengthwise direction of the strip). The group of m transducers is equivalent to a single transducer, whose size is equal to m times the size of the transducers forming the group. The activation of the transducers 5 of strip 4 takes place starting from the transducers furthest from the surface 6 of part 3 and proceeding to the transducer closest to its surface.

FIG. 1 shows that the width d of acoustic beam 10 transmitted by the group 9 of m transducers increases with the weld depth p. As the group 9 of m transducers is displaced by a constant step following each activation, the redundancy rate, corresponding to the number of times a point defect 11 (of the weld 2 in the present case) is impinged upon by the acoustic beam 10, increases with the depth p. Therefore the probe of FIG. 1 suffers from the disadvantage that it is only possible to inspect part 3 at a reduced speed.

It is possible to conceive other multitransducer probes making it possible to retain a constant redundancy rate, i.e. independent of the depth, so as to obtain a higher inspection speed by simultaneously increasing, when the depth p increases, the number m included in the elements of group 9 of activated transducers and the advance or displacement step of said group. These other multitransducer probes therefore suffer from the disadvantage of requiring very complex electronic control means.

SUMMARY OF THE INVENTION

The object of the present invention is to obviate the aforementioned disadvantages.

The present invention therefore specifically relates to an ultrasonic probe for transmitting ultrasonic beams in the direction of depth points of an object to be inspected of variable depth and/or for receiving the ultrasonic beams from these points in response to other ultrasonic beams supplied thereto. The inventive probe is of the type comprising at least one line of M juxtaposed transmitter and/or receiver ultrasonic transducers oriented towards the object to be inspected and means for activating at least one group of m juxtaposed transducers from among the M transducers and following activation, for displacing, by an integral number of transducers, the activated portion of the probe (formed by m activated transducers) in a given direction, wherein the M transducers have different sizes and are arranged in a monotonic manner in accordance with their sizes in each line. The sizes of the transducers are defined in such a way as to scan the object with a known redundancy rate that is substantially independent of the depth.

The term "ultrasonic probe for transmitting and/or receiving ultrasonic beams" is understood to mean a probe having at least one of the two ultrasonic beam transmission and reception functions.

The term "transmitter and/or receiver ultrasonic transducer" is understood to mean a transducer having at least one of the two ultrasonic transmission and reception functions.

The term "size of a transmitter and/or receiver ultrasonic transducer" is understood to mean the size of each transmitting and/or receiving zone of said transducer along the length of the line of transducers to which it belongs.

The term "transducers arranged in a monotonic manner in accordance with their sizes" is understood to mean transducers arranged in accordance with their increasing or decreasing sizes.

The divergence of an ultrasonic beam is inversely proportional to the size of the transducer transmitting it, so that the variation in the size of the transducer along their line makes it possible to compensate for the increase in the width of the ultrasonic beam with increasing depth.

The use of ultrasonic transducers of variable sizes, determined in such a way as to permit the inspection of an object with a constant redundancy rate and which is independent of the depth, makes it possible to obtain an optimum inspection speed, which is substantially greater than the speeds attainable with the multitransducer probes, while requiring simple and consequently inexpensive electronic control means. Moreover, for a constant inspection quality, i.e. a constant redundancy rate, the probe according to the invention requires far fewer transducers and consequently fewer measurements have to be carried out as compared to the case of known probes, which correspondingly increases the analysis rate. Moreover, the probe according to the invention has a better signal-to-noise ratio than known probes, in which the transducers are all of the same size (this ratio corresponding in the case of transmission to the ratio of the energy propagated by the primary transmission lobe to the energy propagated by the secondary transmission lobes).

According to a special embodiment of the ultrasonic probe according to the invention the M transducers are transmitter-receiver transducers, the activation of the m transducers consisting of a transmission followed by a reception. The activation and displacement means carry out this activation starting from the m smallest transducers in the line and performing the displacement of the activation zone towards the m largest transducers in the line, so that the probe makes it possible to inspect the object in accordance with the echo method, also called the "transmitter-receiver method".

According to another embodiment, the M transducers are transmitter-receiver transducers, and the activation and displacement means activate a group of m transducers starting from the m smallest transducers in the line while making the m activated transducers function as transmitters, followed by the activation of another group of m other transducers starting from the m largest transducers in the line while making these m other transducers function as receivers, and displaces the transmitting zone towards the m largest transducers in the line and the receiving zone towards the m smallest transducers in the line, the probe thus making it possible to inspect the object in accordance with the tandem method.

According to another special embodiment, the number of lines of M transducers is equal to two, one of the lines being formed from transmitter transducers and the other from receiver transducers, said lines being parallel and facing one another on either side of the object, while being oriented with respect to one another in such a way that the largest transducer of one line faces the smallest transducer of the other line. Activation and displacement means are provided for carrying out the activation of one group of m transmitter transducers starting from the m smallest transducers in the corresponding line, followed by the activation of another group of m receiver transducers starting from the m largest transducers in the other line, and for displacing the transmitting zone towards the m largest transducers in the corresponding line and the receiving zone towards the m smallest transducers in the other line. The probe thus permits the inspection of the object in accordance with the transmission method.

According to another embodiment, the number of lines of M transducers is equal to two, one of the lines being formed from transmitter transducers and the other from receiver transducers, said lines being non-parallel, while being located on the same side of the object and arranged so that their respective smallest transducers face one another, and diverging from said smallest transducers. The activation and displacement means are provided for activating a group of m transmitter transducers starting from the m smallest transducers in the corresponding line, followed by the activation of another group of m receiver transducers starting from the m smallest transducers of the other line, and for displacing said transmitting group and said receiving group towards the m largest transducers in the respective lines. The probe thus makes it possible to inspect the object in accordance with the reflection method, also called the "separate transmitter-receiver method".

According to a first type of said special embodiment, the activation and displacement means simultaneously activate the transducers of each group of m transducers.

According to a second type of said special embodiment, the activation and displacement means activate the transducers of each group of m transducers progressively and sequentially starting from one of them, with activation delays which are independent of the position of said group in its line.

According to a preferred feature of the ultrasonic probe according to the invention, the sizes of the M transducers of each line form an arithmetic progression.

Finally, according to another embodiment of the invention, the integral number of transducers by which each group of m transducers is displaced, exceeds the number m and the activation and displacement means serve to vary the number m on each activation, so that the ultrasonic beam transmitted by each group and/or received by said group has a size which is independent of the depth.

With this latter embodiment, the electronic control means of the transducers are slightly more complicated than those used with a probe according to the invention operating with a constant number m of active transducers, but these control means are simpler than the electronic control means of the prior art probes which, in order to retain a constant redundancy rate, require not only a number M of transducers with the depth, but also a displacement of the group of m transducers with said depth.

BRIEF DESCRIPTION OF THE DRAWINGS

The invention is described in greater detail hereinafter relative to non-limitative embodiments and with reference to the drawings (apart from FIG. 1 which has already been described and diagrammatically shows a prior art ultrasonic multitransducer probe), wherein:

FIGS. 4 to 6 are diagrams illustrating other embodiments of the ultrasonic probe according to the invention, respectively making it possible to inspect a part by the "tandem", "transmission", and "reflection" methods.

DETAILED DESCRIPTION OF THE PREFERRED EMBODIMENTS

Figure 2:
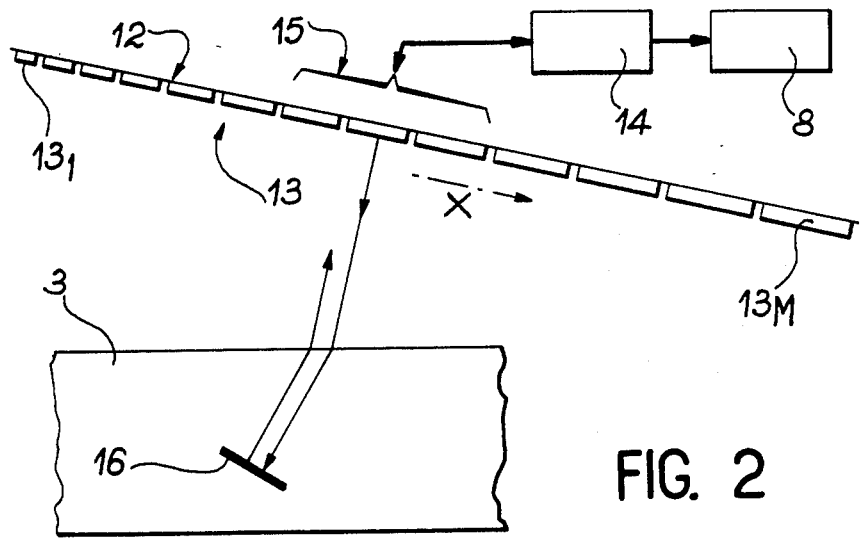
FIG. 2 shown diagrammatically a special embodiment of the ultrasonic probe according to the invention permitting the inspection of a part by the so-called "echo" method.

FIG. 2 diagrammatically shows an embodiment of the ultrasonic probe according to the invention making it possible to inspect a part 3 by the "echo" method. This probe comprises a linear strip or line 12 of M ultrasonic transmitter-receiver transducers 13 and electronic means 14 for the control of transducers 13, these means being connected to volume display means 8.

Transducers 13 have sizes which differ from one another, varying in accordance with an arithmetic progression. The transducers 13 are arranged in order of increasing size on strip 12 and the latter is kept inclined relative to part 3 by way of a support (not shown) such that the smallest transducer $13_1$ is the furthest from part 3.

The control means 14 serves to activate a group 15 of m juxtaposed transducers among the M transducers, starting from the m smallest transducers of the strip 12, and to displace, following each activation, the group 15 by an integral number of transducers, e.g. by one transducer, in the direction of the m largest transducers, until all the transducers in the strip have been activated in this way. In other words, with m equal to 3 for example, a first group of transducers comprising the first, second and third transducers of strip 12 is activated. These transducers are controlled to act as transmitters, so as to produce an ultrasonic beam which impinges on part 3, after which they are controlled to act as receivers, so as to receive a possible echo from a defect 16 in part 3. Then a second group of transducers formed by the second, third and fourth transducers of strip 12 is activated and so on.

It can be shown that the transducers, whose sizes vary in accordance with an arithmetic progression, make it possible to inspect part 3 with a redundancy rate which is independent of the depth of the locus being inspected. Thus, the diameter d of the ultrasonic beam (for a drop of 6dB) is linked to the depth p of an inspected point by the following relation:

$$d = \lambda(K_1 + K_2 p)/D \quad (1)$$

in which $\lambda$, $K_1$, $K_2$ and D respectively designate the wavelength of the ultrasonic beam, a first constant, a second constant and the dimension in the incidence plane of the transducer equivalent to the group of m transducers. On considering the displacement $\Delta x$ of said group by one transducer, it is possible to write as a first approximation:

$$\Delta x = D/m \quad (2)$$

A progression of $\Delta x$ long axis X defined by strip 12, leads to a depth progression $\Delta p$, such that:

$$\Delta p = K_3 \Delta x \quad (3)$$

in which $K_3$ is a constant. The condition of the constant overlap rate implies:

$$\Delta p = K_4 d \quad (4)$$

in which $K_4$ is a constant. The aforementioned relations (1) to (4) make it possible to write:

$$D^2 = K_4 m \lambda (K_1 + K_2 p)/K_3 \quad (5)$$

A differentiation of relation (5) makes it possible to obtain the variation $\Delta D$ of the dimension D of the transducer equivalent to the group of m transducers:

$$\Delta D = K_2 K_4 / \lambda \quad (6)$$

Figure 1:
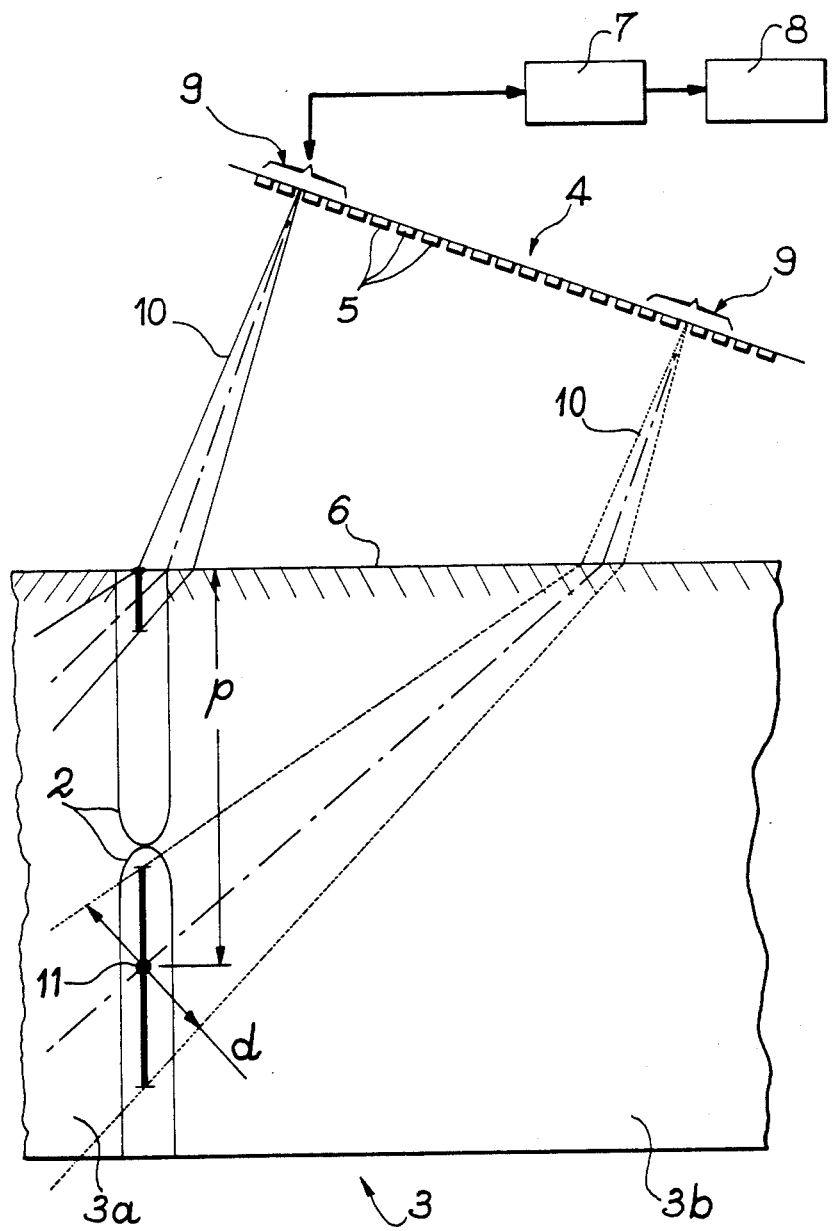

This variation $\Delta D$ is equal to the difference between the size $\Delta x_{n+m}$ of the transducer of rank n+m in strip 12 and the size $\Delta x_n$ of the transducer of rank n in said strip. Thus, the size of the transducer of rank n in the strip can be written:

$$\Delta x_n = a_1 + n a_2 \quad (7)$$

in which $a_1$ and $a_2$ are constants. The latter formula (7) can also be written:

$$\Delta x_n = \Delta x_1 + (n-1)a_2 \quad (8)$$

which shows that the transducers, whose sizes form an arithmetic progression, make it possible to obtain a constant redundancy rate, i.e. it is independent of the depth. The size of the transducers increases with the depth, but therefore the size of the ultrasonic beam increases less rapidly with depth than the size of the ultrasonic beam produced by the prior art probe and described relative to FIG. 1.

The constants $a_1$ and $a_2$ of formula (7) can be determined as a function of the shape of part 3 and the position of strip 12 relative to said part.

The strip 12 with transducers of different sizes can be formed from a ceramic strip, in which cuts are made at predetermined intervals by using a diamond saw or a wire saw, so as to form the transducers and electrically and mechanically insulate them from one another. For example, for a frequency of 1 MHz, in order to cover a depth of 250 mm with the same number n equal to 6 transducers per group and for the same zero depth, ultrasonic beam dimension of 7.5 mm, it is necessary in the case of the known probe of FIG. 1 to have a strip of 54 transducers, 5 mm long and with 48 control or inspection steps. The ultrasonic beam diameter is 54 mm at a depth of 250 mm. In contrast, in the case of the probe according to the invention as shown in FIG. 2, it is merely necessary to have a strip of 32 elements, whose length ranges between 5 and 13.4 mm and with 26 control or inspection steps, the diameter of the beam at a depth of 250 mm being 20 mm.

Thus, this example makes it very clear that the invention provides a considerable advance over the prior art.

The probe described relative to FIG. 2 can operate as a non-focused probe, the control means 14 then serving to simultaneously activate the transducers 13 of group 15 during each activation.

Figure 3:
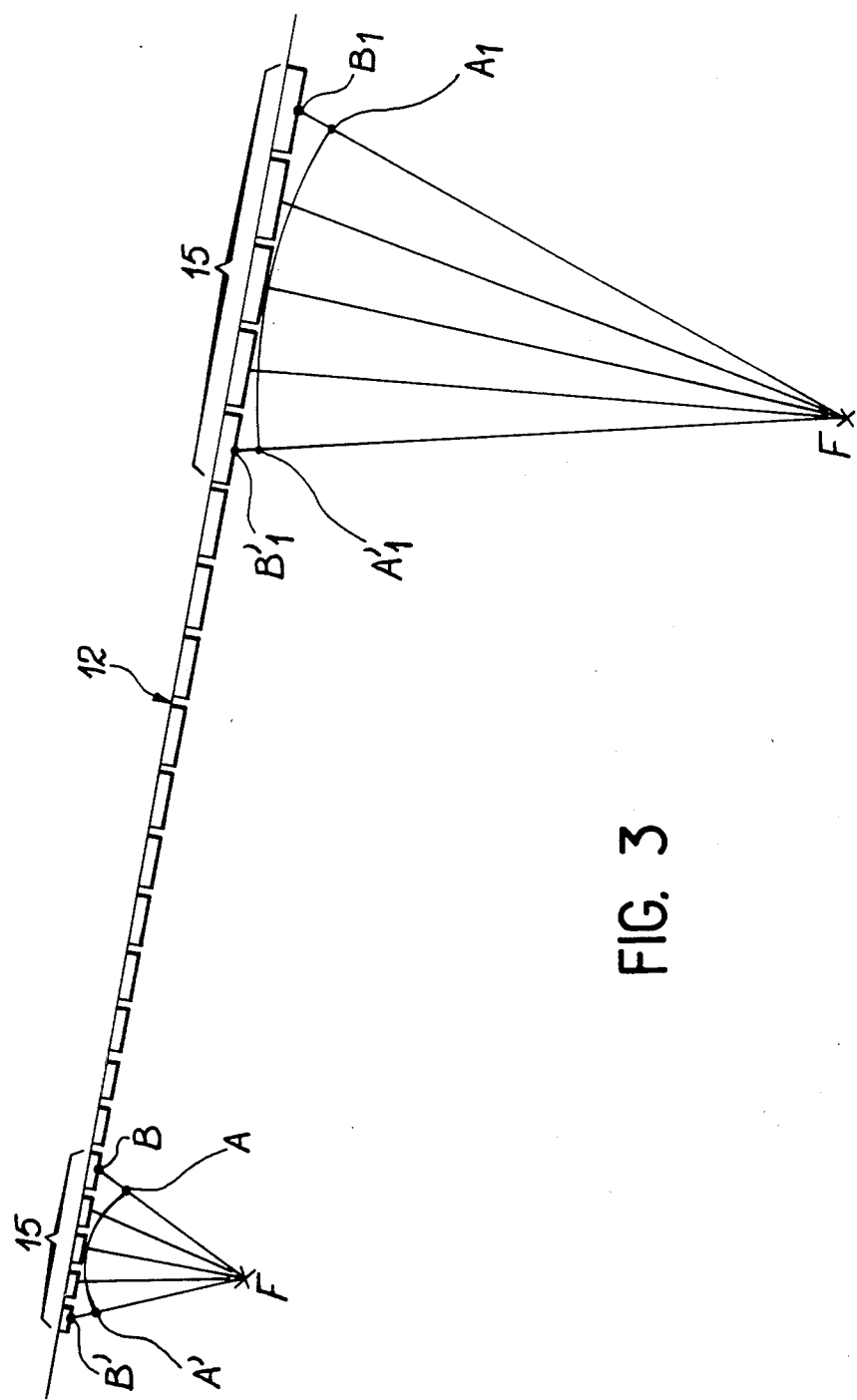
FIG. 3 is an explanatory diagram of the possibility of using focused transducers in the present invention.

FIG. 3 envisages the case where the transducer equivalent to group 15 of m transducers is focused. The control means 1 (not shown in FIG. 3) are then provided for activating the transducers of group 15 in a progressive and sequential manner starting from one transducer. For example, for a given position of group 15 with an uneven number m of transducers, e.g. m=5, between the signals corresponding to the central transducer of group 15 and the signals of the other transducers in said group delays are introduced which increase on moving away from the central transducer, these delays also being symmetrical to the transducer. FIG. 3 shows maximum delays by segments AB and A'B' which are equal for a given position of group 15 and segments $A_1 B_1$ and $A'_1 B'_1$ which are equal for another position of said group 15. It can be shown that in the considered case of transducers whose sizes increase in an arithmetic progression, the maximum delay $\Delta$ corresponding to the transducers furthest from the central transducer of group 15 is independent of the depth. Thus, by maintaining delay $\Delta$ constant, no matter what the position of group 15 in the strip 12 of transducers, the depth of the focusing point F increases with the size of the activated transducers, i.e. as group 15 is displaced towards the m largest transmitters. The refraction is abstracted in FIG. 3, because it only introduces a multiplication factor into the calculations.

Figure 4:
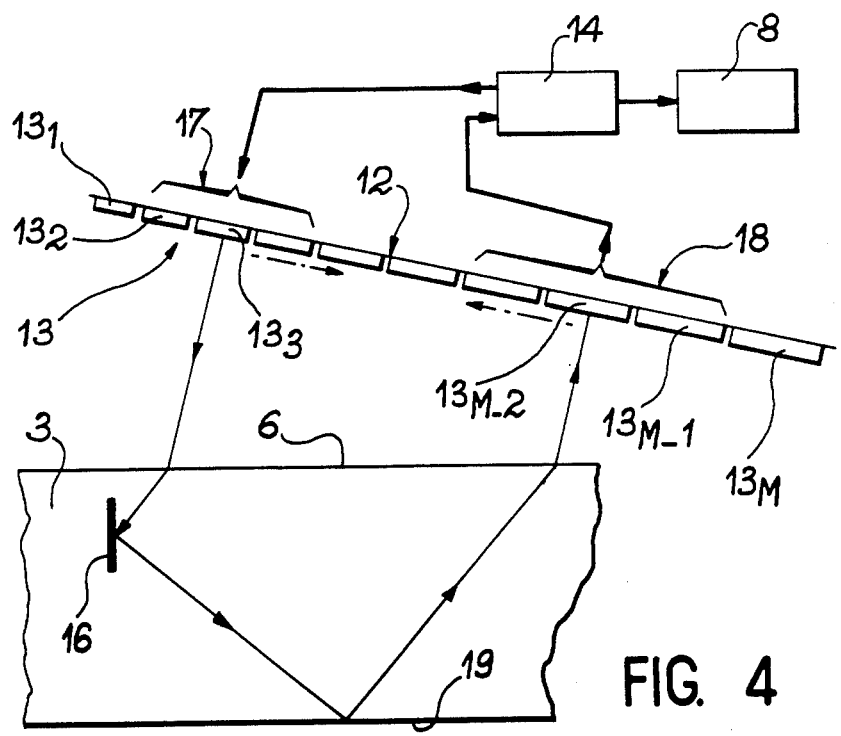

FIG. 4 diagrammatically shows another embodiment of the ultrasonic probe according to the invention making it possible to inspect a part 3 by the "tandem" method. The probe of FIG. 4 is constituted in the same way as that described relative to FIG. 2, except with respect to the control means 14, which serves to activate a group 17 of m transducers starting from the m smallest transducers of the strip 12, by operating these m transducers as transmitters, followed by the activation of another group 18 of m other transducers starting from the m largest transducers of strip 12, while making said m other transducers function as receiver. Control means 14 displaces group 17 towards the m largest transducers of the strip and displaces the other group 18 towards the m smallest transducers of the strip. In other words, for a number m=3, for example, the control means activates firstly the three first transducers $13_1$, $13_2$, $13_3$ of the strip as transmitters and the last three transducers $13_{m-2}$, $13_{M-1}$, $13_M$ of said strip as receivers. Then, with a displacement of e.g. one transducer, the transducers of rank 2, 3 and 4 are activated as transmitters and the transmitters of rank M−3, M−2, and M−1 receivers, and so on until the last three transducers of the strip have been activated as transmitters and the first three transmitters of the strip have been activated as receivers. For a given position of transducer group 17, there is a transmission of an ultrasonic beam which propagates through part 3, reflects from a possible defect 16 located in said part and disposed perpendicular to the surface 6 thereof, reflects from the bottom 19 of part 3 and is then intercepted by the other transducer group 18, which makes it possible to detect the defect 16.

FIG. 5 diagrammatically shows another embodiment of the ultrasonic probe according to the invention, which makes it possible to inspect part 3 in accordance with the so-called "transmission" method. The ultrasonic probe of FIG. 5 comprises a linear strip or line 20 and another linear strip or line 21 of ultrasonic transducers 13, these two strips being identical to the strip 12 described relative to FIG. 2, with the exception that in the present case the transducers of strip 20 function as ultrasonic transmitters and the transducers of the other strip 21 function as ultrasonic receivers. Strip 20 is placed on one side of part 3, said transducers being directed towards the part and mounted on a support (not shown) so as to be disposed relative to part 3 such that the smallest transducer of strip 20 is the furthest from part 3. The other strip 21 is arranged on the other side of part 3, its transducers also being directed towards the part. This other strip 21 is mounted on another support (not shown), parallel to strip 20 and in such a way that the largest transducer of strip 21 faces the smallest transducer of strip 20.

The probe shown in FIG. 5 also comprises control means 14 for activating a group 22 of m transmitter transducers of strip 20 starting from the m smallest transducers thereof, followed by the activation of another group 23 of m receiver transducers of the other strip 21 starting from the m largest transducers of said other strip, and for effecting the displacement of the group 22 towards the m largest transducers of strip 20 and the displacement of the other group 23 towards the m smallest transducers of the other strip 21. In other words, if e.g. m=3, the group 22 formed by the first three smallest transducers of strip 20 and the group 23 formed by the three largest transducers of the other strip 21 are firstly activated, then each group is displaced by the same number of transducers, e.g. one transducer. Then the three following transducers respectively of strips 20 and 21 are activated and so on. For a given position of transducer 22 and the other transducer group 23, an ultrasonic beam 24 is transmitted by group 22 and propagated through part 3, in which the beam may encounter a defect 16. The latter is detected when it is in the area common to beam 24 transmitted by group 22 and to the spatial reception zone 25 of the other receiver transducer group 23 and can be observed on the display means 8 connected to the control means 14.

FIG. 6 diagrammatically shows another embodiment of the ultrasonic probe according to the invention making it possible to inspect part 3 by the so-called "reflection" method. The probe of FIG. 6 comprises strip 20 and the other strip 21 or described relative to FIG. 5, except that the strips are arranged in a different way. The transducers of strips 20 and 21 respectively operate as ultrasonic transmitters and ultrasonic receivers.

The two strips 20 and 21 are arranged on the same side of part 3 and are mounted on a support (not shown) so as to be inclined relative to part 3, their smallest transducers being the transducers which are furthest from part 3, such that the respective planes of strips 20 and 21 form an obtuse angle $\alpha$ between them and such that the two strips diverge by a small acute angle $\beta$ starting from the smallest transducers thereof. The ultrasonic probe of FIG. 6 also comprises control means 14 for activating a group 22 of m transmitter transducers starting from the m smallest transducers of strip 20, followed by the activation of another group 23 of m receiver transducers, starting from the m smallest transducer of the other strip 21, and for effecting the displacement of groups 22 and 23 towards the m largest transducers of their respective strips.

In other words, if e.g. m=3, groups 22 and 23 respectively formed by the first three smallest transducers of each strip are firstly activated, these groups being displaced by e.g. one transducer in the corresponding strips and so on, until the last three transducers of each of the two strips have been activated. For a given position of the respective groups 22 and 23 of transmitting and receiving transducers, an ultrasonic beam is transmitted by group 22 and is propagated through part 3, in which the beam may encounter a defect 16 located in the plane midway between the respective strips 20, 21, and by which the ultrasonic beam is reflected in the direction of the other group 23 of receiver transducers, which makes it possible to detect the defect. The defect can then be observed on the display means 8 connected to the control means 14.

Obviously, in the probes shown in FIGS. 4 to 6, the transducers respectively equivalent to the groups of m transducers could be focused transducers. Moreover, for the probes described relative to FIGS. 2 to 6, the integral number of transducers by which each group of m transducers is displaced could exceed the number m, the control means then serving to vary the number m on each activation, in such a way that the ultrasonic beam transmitted by a group of m transmitter transducers maintains a constant width, no matter what the depth.

In the aforementioned embodiments, the number m of activated transducers is the same upon transmission and upon reception. The invention also covers cases where these numbers differ, which makes it possible to obtain different beam diameters upon transmission and upon reception.

Furthermore, in all the embodiments described, the scanning of the transducers takes place from the m smallest to the m largest transducers. However, the invention also covers cases where the scanning direction is reversed, or even varied over a period of time, the invention relating to the size of the beam and not to the way in which it scans the parts to be inspected.

What is claimed is:

1. An ultrasonic probe for transmitting ultrasonic waves in the direction of an object having points of variable depth to be inspected and for receiving the ultrasonic waves reflected from said points in response to impingement of said transmitted ultrasonic waves thereon, comprising a first plurality of M juxtaposed ultrasonic transducers arranged along a first line and directed toward said object, M being an integer, and control means for selectively activating successive groups of m juxtaposed transducers from among said first plurality to form successive zones of activation, where m<M and m is an integer, and for progressively displacing said zone of activation along said first line in a predetermined direction during successive activations for accomplishing scanning of said object, said displacement having a magnitude corresponding to the total dimension along said first line of an integral number of juxtaposed transducers, wherein each of said first plurality of transducers has a different dimension along said first line and said transducers of said first plurality are arranged in order of increasing dimension, said dimension along said first line being selected such that a predetermined redundancy rate is attained during scanning of said object, which redundancy rate is substantially independent of the depth of said point to be inspected, said redundancy rate being defined as the number of successive activations during which said point is impinged upon by said transmitted ultrasonic waves.

2. The ultrasonic probe as defined in claim 1, wherein each of said first plurality of M transducers is capable of transmitting or receiving ultrasonic waves in response to activation by said control means, and said activated transducers are controlled to act as transmitters at a first instant of time and then to act as receivers at a second instant of time, said second instant of time corresponding to the time of arrival of an ultrasonic wave transmitted during said first instant of time and then reflected from a defect in said object.

3. The ultrasonic probe as defined in claim 2, wherein said activated transducers form a zone of activation, said zone of activation being progressively displaced by said control means from a group of m smallest juxtaposed transducers to a group of m largest juxtaposed transducers.

4. The ultrasonic probe as defined in claim 1, wherein each of said first plurality of M transducers is capable of transmitting or receiving ultrasonic waves in response to activation by said control means, said control means activating a first group of m juxtaposed transducers to act as transmitters at a first instant of time and activating a second group of m juxtaposed transducers to act as receivers at a second instant of time, said second instant of time corresponding to the time of arrival of an ultrasonic wave transmitted during said first instant of time and then reflected from a defect in said object.

5. The ultrasonic probe as defined in claim 4, wherein said transducers activated to transmit form a first zone of activation and said transducers activated to receive form a second zone of activation, said first zone of activation being progressively displaced by said control means from a group of m smallest juxtaposed transducers to a group of m largest juxtaposed transducers and said second zone of activation being progressively displaced by said control means from a group of m largest juxtaposed transducers to a group of m smallest juxtaposed transducers.

6. The ultrasonic probe as defined in claim 1, further comprising a second plurality of M juxtaposed ultrasonic transducers arranged along a second line and directed toward said object, wherein each of said second plurality of transducers has a different dimension along said second line and said transducers of said second plurality are arranged in order of decreasing dimension, such that largest transducer of said first plurality faces a smallest transducer of said second plurality, said control means activating successive groups of m juxtaposed transducers of said first plurality to act as transmitters and activating successive groups of m juxtaposed transducers of said second plurality to act as receivers, said first and second lines being parallel, and said transducers of said second plurality being arranged to receive ultrasonic waves transmitted by said activated transducers of said first plurality andw reflected from defects in said object.

7. The ultrasonic probe as defined in claim 6, wherein said transducers activated to transmit form a first zone of activation and said transducers activated to receive form a second zone of activation, said first zone of activation being progressively displaced by said control means from a group of m smallest juxtaposed transducers to a group of m largest juxtaposed transducers of said first plurality and said second zone of activation being progressively displaced by said control means from a group of m largest juxtaposed transducers to a group of m smallest juxtaposed transducers of said second plurality.

8. The ultrasonic probe as defined in claim 1, further comprising a second plurality of M juxtaposed ultrasonic transducers arranged long a second line and directed toward said object, wherein each of said second plurality of transducers has a different dimension along said second line and said transducers of said second plurality are arranged in order of increasing dimension, such that a smallest transducer of said first plurality faces a smallest transducer of said second plurality, said control means activating successive groups of m juxtaposed transducers of said first plurality to act as transmitters and activating successive groups of m juxtaposed transducers of said second plurality to act as receivers, said first and second lines being non-parallel, and said transducers of said second plurality being arranged to receive ultrasonic waves transmitted by said activated transducers of said first plurality and reflected from defects in said object.

9. The ultrasonic probe as defined in claim 8, wherein said transducers activated to transmit form a first zone of activation and said transducers activated to receive form a second zone of activation, said first zone of activation being progressively displaced by said control means from a group of m smallest juxtaposed transducers to a group of m largest juxtaposed transducers of said first plurality and said second zone of activation being progressively displaced by said control means from a group of m smallest juxtaposed transducers to a group of m largest juxtaposed transducers of said second plurality.

10. The ultrasonic probe as defined in claim 8, wherein a distance separating said smallest transducers of said first and second pluralities is less than a distance separating the largest transducers of said first and second pluralities.

11. The ultrasonic probe as defined in claim 1, wherein said control means simultaneously activates the transducers in an activated group of m juxtaposed transducers.

12. The ultrasonic probe as defined in claim 1, wherein said control means activates the transducers of each successive group of m juxtaposed transducers in a sequential manner starting from one of said transducers, with activation delays which are independent of the position of said group in said first plurality.

13. The ultrasonic probe as defined in claim 1, wherein the dimensions along said first line of said first plurality of M transducers are determined in accordance with an arithmetic progression.

14. The ultrasonic probe as defined in claim 1, wherein said integral number of transducers by which each group of m juxtaposed transducers is displaced exceeds the number m, and said control means serve to vary the number m for each activation such that the ultrasonic beam transmitted by each group has a dimension which is independent of the depth of said point to be inspected.

* * * * *